(12) United States Patent
Lockery et al.

(10) Patent No.: US 6,533,723 B1
(45) Date of Patent: Mar. 18, 2003

(54) MULTIPLE-LINK CABLE MANAGEMENT APPARATUS

(75) Inventors: Donald R. Lockery, Germantown, WI (US); David G. Hernke, Sussex, WI (US)

(73) Assignee: GE Marquette Medical Systems, Inc., Milwaukee, WI (US)

( * ) Notice: Subject to any disclaimer, the term of this patent is extended or adjusted under 35 U.S.C. 154(b) by 9 days.

(21) Appl. No.: 09/649,438

(22) Filed: Aug. 25, 2000

(51) Int. Cl.[7] .................................................. A61B 5/00
(52) U.S. Cl. ........................ 600/300; 128/904; 128/897
(58) Field of Search .................................. 600/300, 301, 600/345, 508, 483, 485; 702/91, 85; 128/897–925; 710/20, 22, 65, 300; 340/3.1, 573.1

(56) References Cited

U.S. PATENT DOCUMENTS

| | | | | |
|---|---|---|---|---|
| 5,375,604 A | * | 12/1994 | Kelly et al. | ................. 600/483 |
| 5,839,094 A | * | 11/1998 | French | ......................... 702/85 |
| 6,050,940 A | * | 4/2000 | Braun et al. | ................. 600/300 |
| 6,083,156 A | * | 7/2000 | Lisiecki | ....................... 600/301 |
| 6,112,224 A | * | 8/2000 | Peifer et al. | .................. 340/3.1 |
| 6,259,944 B1 | * | 7/2001 | Margulis et al. | ............ 128/903 |

OTHER PUBLICATIONS

Anthony Gribben and David G. Hernke; "An 8–Channel, 18 Bit Data Acquisition System"; Abstract: 5 pages with 8 Figures (9 pages total).

* cited by examiner

*Primary Examiner*—Eric F. Winakur
*Assistant Examiner*—David J. McCrosky
(74) *Attorney, Agent, or Firm*—Michael Best & Friedrich LLP

(57) ABSTRACT

A cable management and data acquisition method and apparatus to store system data and data from activity sensors when the sensors are disconnected from a monitoring system. The apparatus includes a housing, a first connection port operable to receive information from one or more activity sensors, a device interface coupled to the first connection port, a non-volatile memory coupled to the device interface; and an output port coupled to the device interface. The cable management and data acquisition apparatus may also include a digital-to-analog converter to convert analog signals from sensors to digital signals. Preferably, the device interface is an application specific integrated circuit ("ASIC") that communicates with a signal processor in the monitoring processor. The signal processor responds to commands or messages from the monitoring processor and reads data from and writes data to the memory in the cable management and data acquisition apparatus through the ASIC. The cable management and data acquisition apparatus prevents the loss of patient data when a patient monitoring system is disconnected from the activity sensors attached to a patient, such as might occur when a patient is moved from one location to another. Data stored in the memory of the apparatus can be readily retrieved when the patient arrives to the new location so as to maintain a record of identification data and permit the tracking of trends.

12 Claims, 14 Drawing Sheets

MULTIPLE-LINK CABLE MANAGEMENT APPARATUS

The present invention relates to methods and devices used to monitor the activity of a living subject such as a human patient. More particularly, the invention relates to patient monitoring systems that have multiple sensors with corresponding cables or similar communication links that are connected to monitoring equipment.

Patient monitoring systems generally include a plurality of specialized sensors. Each sensor is designed to measure a specific activity and generate a signal representative of that activity. The signals are transmitted over cables or similar signal carriers to monitoring equipment that processes the signals and generates an output, often in the form of a multiple-component graphical image that is displayed on a monitor such as a CRT, flat panel display, or similar device. A typical patient monitoring system may include many sensors and associated cables. The sensors used might include a blood pressure sensor, a blood oxygenation sensor, an ECG (electrocardiogram) sensor, a respiration sensor, a temperature sensor, and a thermodilution cardiac output (CO) sensor.

Generally, information from the sensors is recorded in a large, usually stationary monitoring device. This method of storing information poses a problem when a patient must be moved. Because a stationary monitoring device is not readily moved, moving a patient requires disconnecting the numerous cables from the device. This interrupts monitoring of the patient. In order to maintain patient monitoring, the patient may be connected to a portable monitoring device. This requires reconnecting the numerous cables to the portable device. This is not an easy task and often results in a tangled mess of cords (sometimes referred to as "spaghetti"). Of course, even when connected to a portable device, information from the period of time when the patient was not connected to either the portable unit or the stationary unit is lost. Trend data from the stationary data device is also lost. Lastly, since there presently is no way to transfer such data automatically, patient identification data must be manually reentered into the portable device.

Other difficulties associated with moving a patient and monitoring his or her biological activity relate to the portable monitoring devices themselves. Portable units are generally difficult to use and expensive. Cost is a large problem because capital equipment ownership is generally assigned on a department-by-department basis. Thus, transferring portable equipment from one department to another within a care facility often causes administrative difficulties. In addition, some portable units are less than satisfactory because of their small monitor size and limited capabilities. Thus, there is a need for improvements to patient monitoring systems that permit patients to be moved with less difficulty and loss of data.

SUMMARY OF THE INVENTION

The present invention provides a relatively easy and low cost method and apparatus for reducing the loss of data when moving a patient from one monitoring device to another. The invention may be implemented in a cable management and data acquisition system that is designed to be coupled between the leads from activity sensors and a patient monitoring device. The cable management and data acquisition system has a housing with one or more connection ports. Each port is designed to be connected to activity sensors, such as ECG sensors, blood pressure sensors, temperature sensors, and the like. The connection ports receive the information from the sensors and deliver it to a device interface. The device interface is coupled to a non-volatile memory, which is used to store patient data and data from the sensors. The device interface is also connected to an output port through which the device interface sends data to a monitoring processor and from which the device interface receives commands. Preferably, the device interface is an application specific circuit and communicates information according to a serial data bus protocol. Data from the sensors is converted to a digital format, as necessary, by an analog-to-digital converter coupled between the connection ports and the device interface.

The size of the memory in the system can be changed depending on the end use of the system. If a user requires storage of trend data and histories, the system is equipped with a relatively large memory. The system is equipped with a smaller memory when monitoring other types of information. Regardless of the size of the memory used, the system uses the same scheme to access data in the memory.

The invention provides a method of storing patient data. The method includes gathering data from at least one sensor, generating a write command with a monitoring processor, and processing the write command in a signal processor. The method also includes locating a non-volatile memory outside the sensor and outside the monitoring processor. Once the write command is processed, the command is executed through the device interface and the gathered data is stored in the non-volatile memory.

Preferably, processing the write command includes the act of breaking the command into command packets. The command packets are then assembled during the processing of the write command. Each command packet typically includes a start-of-packet field, a command field, and a check field. The command packet may also include a data field.

The monitoring processor includes a digital signal processor that has a message program or package that includes a request message sub-package and an algorithm sub-package. The request message sub-package concatenates message packets and validates the address and format of message packets. The message algorithm sets bus commands from a command table to perform the required read or write operation.

As is apparent from the above, it is an advantage of the present invention to provide a method and apparatus for storing data from patient monitoring sensors. Other features and advantages of the present invention will become apparent by consideration of the detailed description and accompanying drawings.

DETAILED DESCRIPTION

Figure 1:
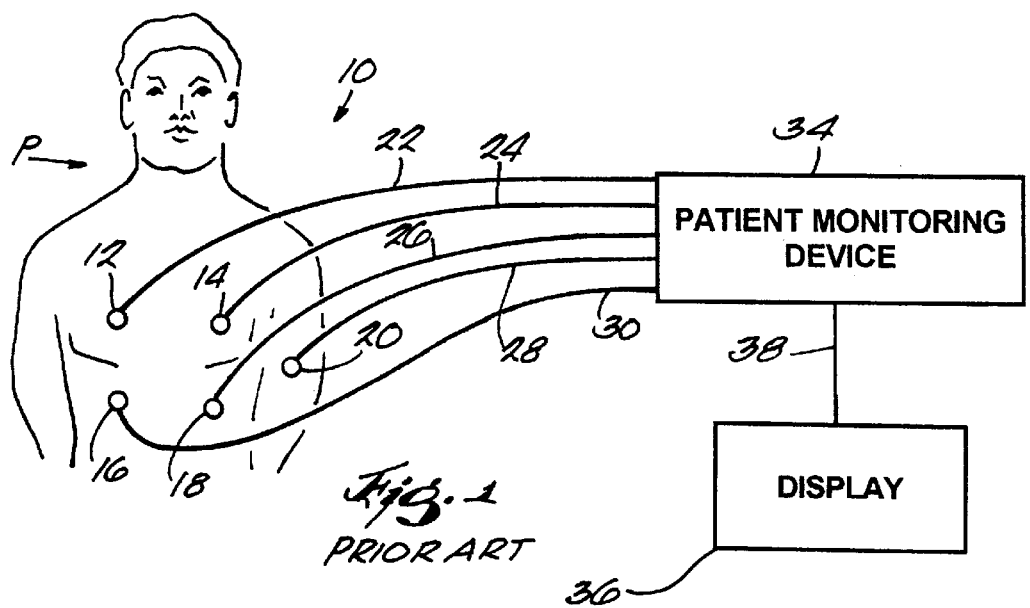
FIG. 1 is a schematic diagram of a known patient monitoring system.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIG. 1 illustrates a known patient monitoring system 10. The monitoring system 10 includes a plurality of sensors 12, 14, 16, 18, and 20, which are connected to a patient P. Each of the sensors is coupled by communication links 22, 24, 26, 28, and 30 to a monitoring processor 34. The monitoring processor 34 processes the signals from the sensors and generates an image signal, which is delivered to a display 36 over a communication link 38. The image on the display is part of graphical user interface (which provides information and through which selections by the user may be input to the monitoring processor 34). A drawback of systems such as the one shown in FIG. 1 is that when a patient is moved multiple sensors must be disconnected from the monitoring processor 34. This causes a significant loss of patient data, particularly data related to parameter trends (e.g., ECG trends,) patient identification data, and configuration and identification information for the devices or sensors connected to the monitoring processor 34.

Figure 2:
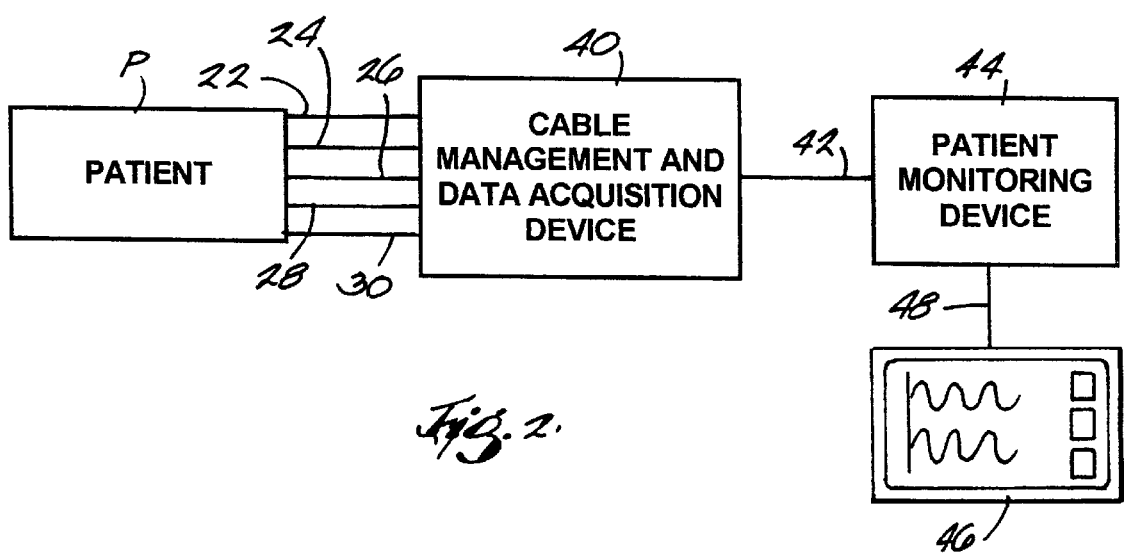
FIG. 2 is a schematic illustration of a cable management and data acquisition system of the invention.

FIG. 2 illustrates a cable management and data acquisition system ("CMADAS") 40 connected to the communication links 22–30 from the patient P (shown schematically). A communication link 42 connects the CMADAS 40 to a monitoring processor 44. The monitoring processor 44 is coupled to a monitor 46 via a communication link 48. The CMADAS is positioned between the patient P and the monitoring processor 44 and, as will be discussed in greater detail below, stores data from the patient sensors, data about the sensors, and/or patient data.

Figure 3:
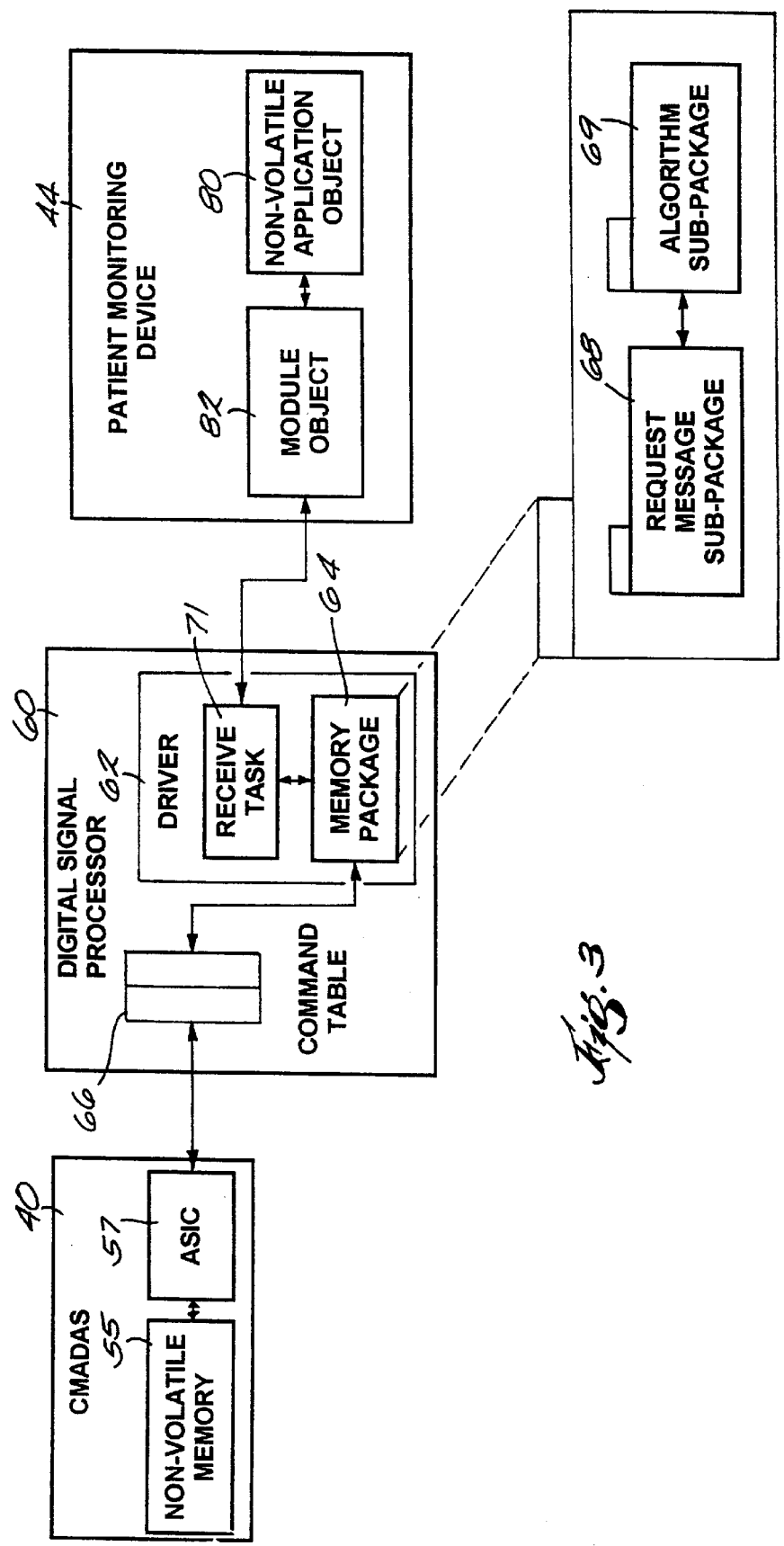
FIG. 3 is a schematic illustration of the cable management and data acquisition system, a digital signal processor, a monitoring processor, and the flow of communication between the three components.

As best seen in FIG. 3, the CMADAS includes data storage 55 in the form of non-volatile memory such as non-volatile RAM or flash memory, but preferably EEPROM. Non-volatile memory is used so that power losses will not affect the data stored in the memory. As will be discussed below, it is preferred that the CMADAS be implemented in at least two different forms: one with a data storage element systems sized to store historical or trended data, and another form suitable for use in applications where historical or trended does not need to be stored. Sometimes the activity being monitored will determine whether trend or historical data is important, but this is not necessarily true in all situations. The data storage 55 is accessed by an application specific integrated circuit ("ASIC") 57. The ASIC 57 acts as a device interface, communicating information according to a serial data bus protocol. Preferably, the serial bus protocol is the GE Marquette Medical Systems, Inc. serial bus protocol ("MSB").

Figure 3A:
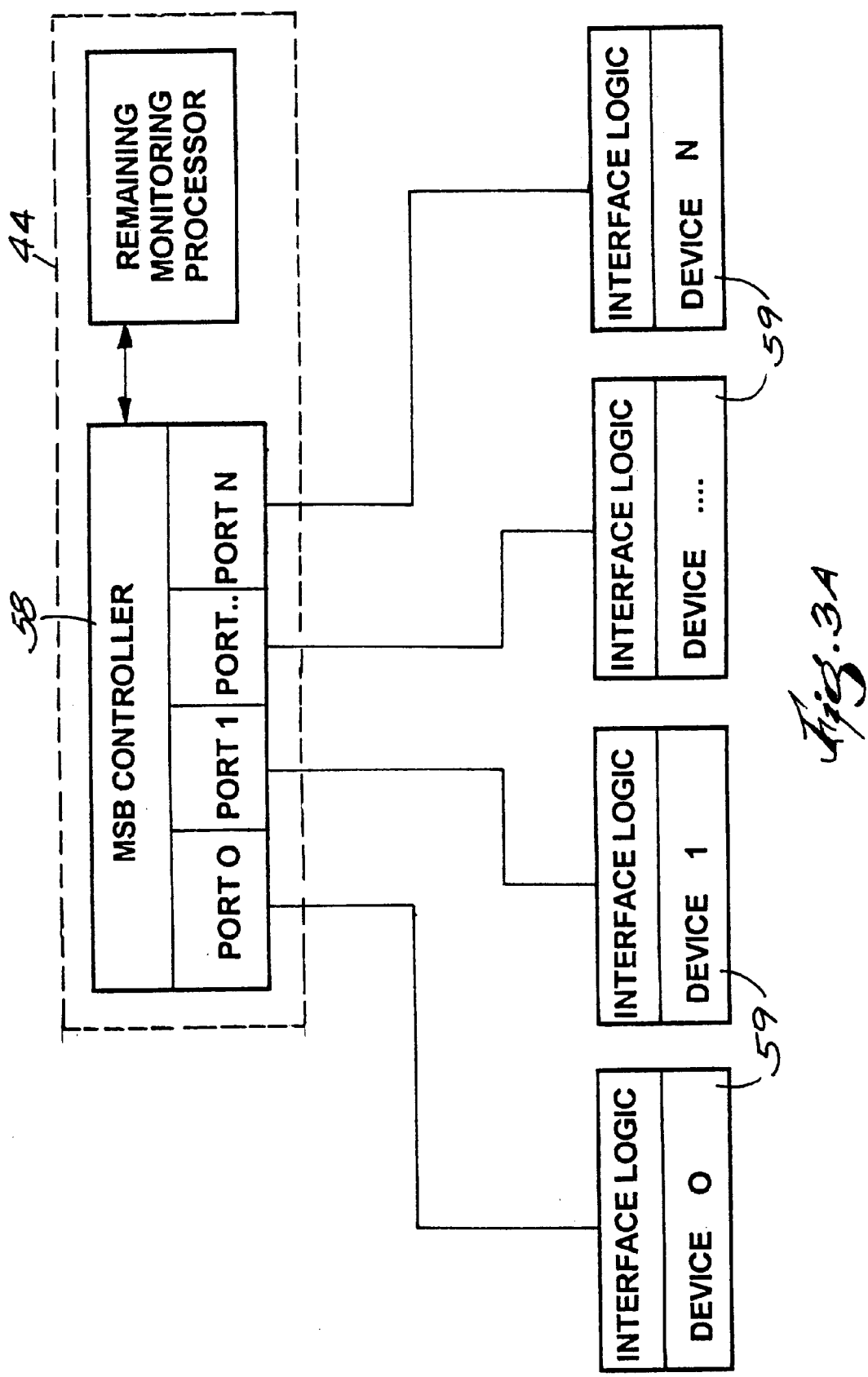
FIG. 3A is a schematic illustration of a bus controller implemented in the monitoring processor shown in FIG. 3.

The MSB provides a hot-swappable, medium-speed serial communications link between the monitoring sensors and the monitoring processor 44. The monitoring processor 44 includes a communications controller 58 (FIG. 3A). Under the MSB architecture, the controller 58 is interfaced to several devices 59 in a star topology. Preferably, devices coupled to the controller 58 interface with the monitoring processor through a communications and power connection having six or less conductors. A modular patient data acquisition system is formed when devices 59 (monitoring sensors) are connected to the monitoring processor through controller 58.

The controller 58 is frame-centered; meaning that it periodically generates a frame interrupt signal. System timing, parameter synchronization, and data acquisition is centered on the frame rate of the controller 58. The controller simulcasts a synchronization check command packet to all devices 59 connected to it at the start of each frame. The controller 59 then performs the command or response communications required by each device. Frames provide a time base that is used by a digital signal processor (discussed below) and the controller 58 to acquire and process data from the devices 59. Preferably, the length of the frames (such as 1.042 ms) is matched to a base sample rate (such as 960 samples/second) used by the devices 59 and is sufficient to acquire data and return analog-to-digital conversion results. If higher sample rates are required, the devices 59 may return multiple samples of a digitized signal in a single frame. The monitoring processor 44 generally filters data and supplies the monitor 46 with streams of data that are a factor of the sampling rate employed. For a sampling rate of 960 samples per second, suitable stream rates include rates of 60, 120, or 240 samples per second.

Preferably, the controller 58 transmits command packets or fragments to the devices 59. The fragments may contain four fields: a 1-byte start-of-packet field, a 1-byte command field, an optional N-byte data field, where N<=240, and a 2-byte check field, such as a cyclical redundancy checking ("CRC") field. Preferably, all bytes are sent with the most significant bit first.

As best seen by reference to FIG. 3, the controller 58 of the monitoring processor 44 sends commands to a digital signal processor 60 (which is preferably placed in the housing of the monitoring processor 44). The signal processor 60 reads and writes to the data storage 55 through the ASIC 57. The signal processor has no knowledge of the contents of the data storage 55. Rather, the signal processors 60 executes the read and write requests received from the monitoring processor 44. The signal processor 60 includes a driver 62 having a memory read/write program or package 64 and a serial data bus command table 66.

The memory package 64 includes a request message sub-package 68 and an algorithm sub-package 69. The request message sub-package 68 responds to requests from the monitoring processor 44. While complete requests are sent from the monitoring processor 44, the controller 58 may break the requests into fragments. The request sub-package 68 assembles and validates request messages and activates the algorithm sub-package 69. The request message sub-package 68 is called each time a message fragment with a data storage address arrives from the monitoring processor 44. A receive task 71 receives all messages from the monitoring processor 44. The receive task 71 scans messages for proper format and address. If a proper format and address are detected, the receive task 71 calls a packet process subroutine, which is also within the request message sub-package 68. The process subroutine concatenates message fragments to form a complete message. A complete message includes an address location and a read request, a write request, or a get information request (return memory size, sector size, and protected blocks). The message formed by the process subroutine is delivered to a pre-processing routine that examines the complete message for proper format and a valid address range.

If an information request is delivered to the signal processor 60, a get-memory-information routine is called. This routine formats a message response, including the requested memory information, and sends a response back to the monitoring processor 44. If a complete and valid read or write message is assembled, the algorithm sub-package 69 is activated and the request message sub-package 68 returns to a dormant state until the next request from the monitoring processor 44 is received. Preferably, the driver 62 operates under a frame-relay protocol and calls the algorithm sub-package 69 during each frame. Once called and activated (for a read or write request), the algorithm sub-package 69 advances its state machine out of a dormant or idle state to an active state. The algorithm sub-package 69 then sets up serial bus commands from the command table 66 to perform the required read or write operation. The algorithm sub-package 69 continues this process frame-after-frame until the requested operation is complete or an error occurs. Once a full response is complete and sent to the monitoring processor 44, the algorithm sub-package 69 returns to an idle state.

The monitoring processor 44 includes an application object 80 that initiates all activity (i.e., read, write, and information requests) and a module object 82 that acts as a message router. Preferably, the communication protocol prohibits the monitoring processor 44 from sending a new request message until the previous request has been fulfilled.

Figure 4:
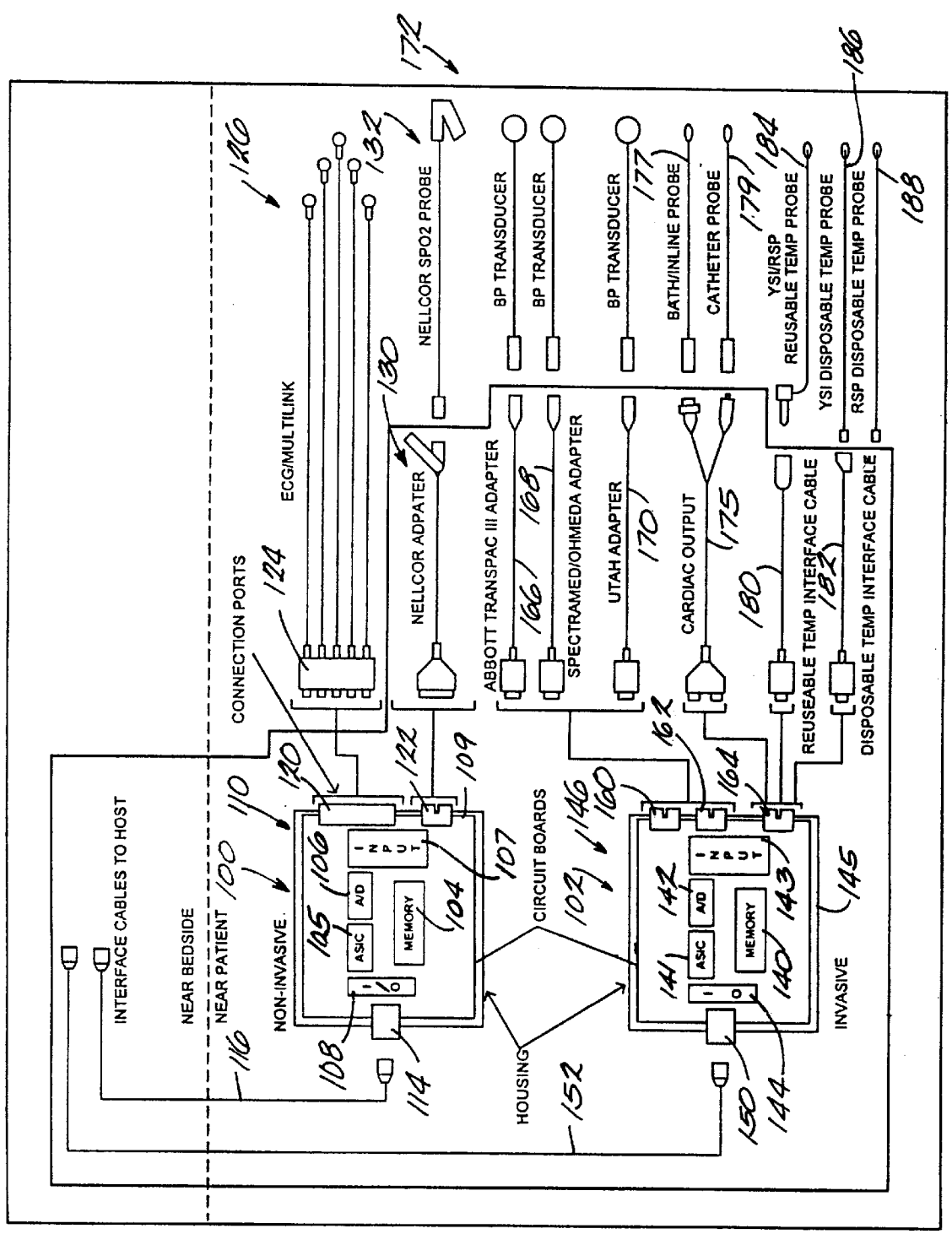
FIG. 4 is a detailed schematic of two cable management and data acquisition systems.

As noted above, it is preferred that the CMADAS 40 be implemented in separate forms to accommodate the memory requirements for different needs to store historical or trend data. Alternatively, the CMADAS could be implemented with parallel and independent systems in a single housing (not shown). FIG. 4 shows two CMADASs 100 and 102. The CMADAS 100 includes memory 104, an ASIC 105, an analog-to-digital ("A/D") converter 106, a sensor input interface 107, and host I/O interface 108. The memory 104 is a relatively large capacity memory to accommodate historical and trend data. Often historical data is important in invasive monitoring applications. Presently, a memory of approximately 128 Kb is suitable for such applications. The memory 104, ASIC 105, A/D converter 106, interface 107, and I/O interface 108 are mounted on a circuit board 109 and placed within a housing 110. The I/O interface 108 is coupled to a port 114 designed to accept a cable 116. The cable 116 is a specific embodiment of the communication link 42 and acts as a pathway between the CMADAS 100 and a monitoring device, such as the monitoring processor 44.

The ASIC 105 receives data from two connection ports 120 and 122. The first connection port 120 is designed to accept pins from an ECG connector 124. The connector 124 is attached to the leads from a plurality of ECG electrodes 126. The connection port 122 includes sockets (not shown) to receive pins from an adapter 130. The adapter 130 is connected to a blood oxygenation sensor 132. The CMADAS 100 receives information from the electrodes 126 and the sensor 132, performs analog-to-digital conversions on the information, as necessary, and transmits the information through the signal processor 60 to the monitoring processor 44. The monitoring processor 44 then instructs the driver 62 to periodically store processed data in the memory 104, according to the access scheme described above.

The CMADAS 102 is similar to the CMADAS 100, but designed with a relatively small memory 140 suitable for applications where trend or historical data need not be recorded. Presently, a memory of approximately 256 bytes of capacity is appropriate for such applications. The CMADAS 102 includes an ASIC 141, an A/D converter 142, an input interface 143, and an I/O interface 144. As with the CMADAS 100, the memory 140, ASIC 141, A/D converter 142, input interface 143, and I/O interface 144 are mounted on a circuit board 145 and placed within a housing 146. The I/O interface 144 is coupled to a port 150 designed to accept a cable 152. The cable 152 is an embodiment of the communication link 42 and acts a pathway between the CMADAS 102 and a monitoring device, such as the monitoring processor 44.

The ASIC 141 receives data from connection ports 160, 162, and 164. The connection port 160 accepts pins from blood pressure sensor adapters 166–170. The adapters 166–170 are attached to the leads of a plurality of blood pressure sensors 172. The connection port 162 accepts pins from an adapter 175. The adapter 175 is connected to two cardiac output probes 177 and 179. Finally, the connection port 164 accepts pins from two temperature probe interfaces 180 and 182. The interface 180 may be connected to a reusable temperature probe 184. The interface 182 may be singularly connected to various disposable temperature probes such as a first disposable probe 186, or a second disposable probe 188.

In a manner that is similar to the operation of the CMADAS 100, the CMADAS 102 receives information from the sensors 172, 177, 179, and 184–188, performs analog-to-digital conversions on the information from the sensors, as necessary, and transmits the information through the signal processor 60 to the monitoring processor 44. The monitoring processor 44 then instructs the driver 62 to periodically store processed data in the memory 140, using the same access scheme used in the CMADAS 100.

Figure 5:
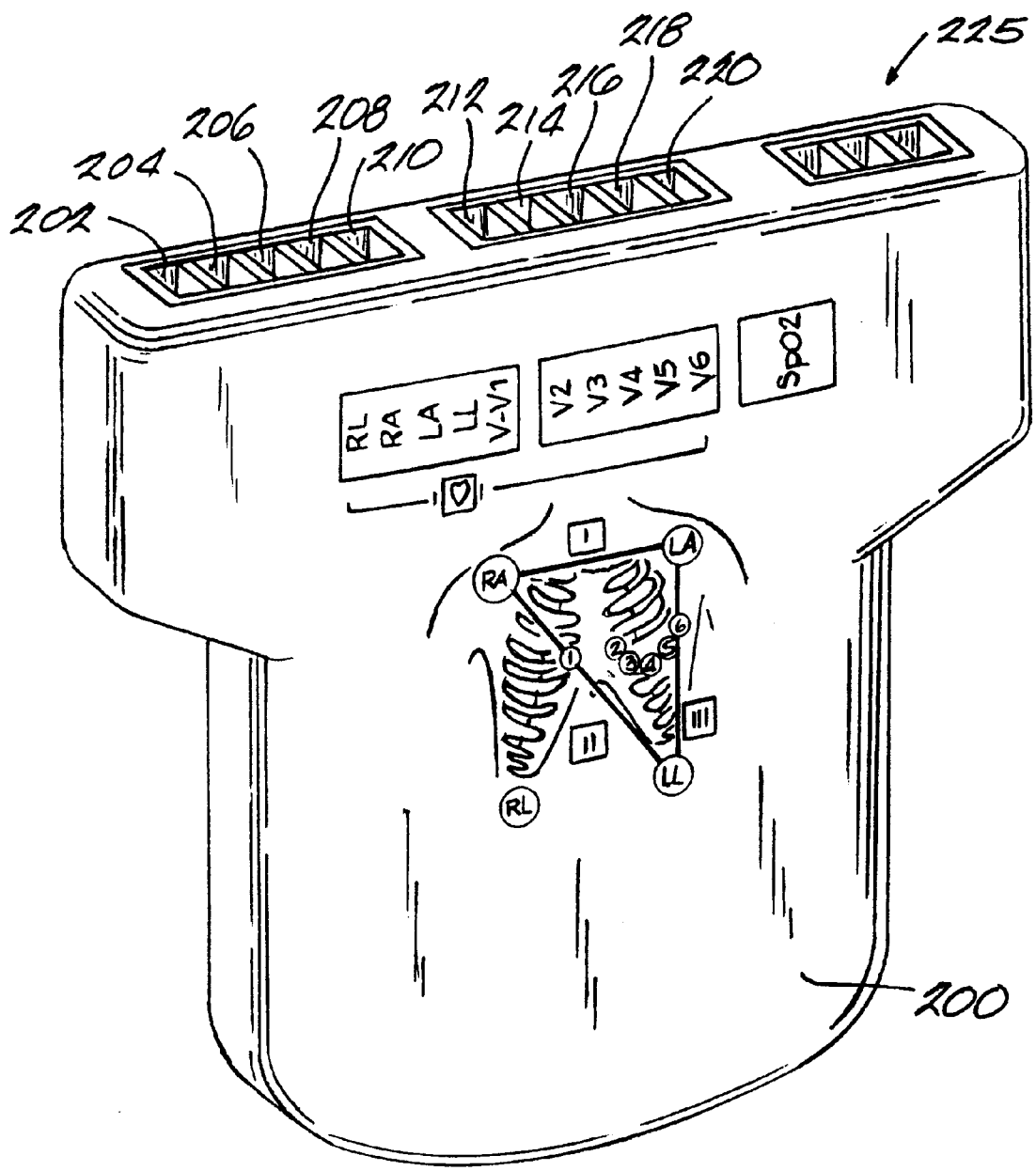
FIG. 5 is a perspective view of a housing for a cable management system of the invention.

FIG. 5 shows an exemplary housing 200 for a CMADAS. The housing 200 is specifically configured for use with a CMADAS designed to store historical and trend data. The housing has connection ports 202–208 for RA (right arm), LA (left arm), RL (right leg), and LL (left leg) electrodes and connection ports 210–220 for a plurality of heart electrodes, V–V1, V2, V3, V4, V5, and V6. The housing also includes an SpO$_2$ port 225. Housings with configurations that are different from the housing 200 are within the scope of the invention as the exact configuration of a housing used in a CMADAS depends on the monitoring application for which it will be used. The housing provides an efficient mechanism to connect the many leads from many sensors to a monitoring processor. The housing may be located near the patient and, as noted above in the discussion of CMADAS 100 and 102, just a single cable needs to be routed from the housing 200 to the monitoring processor. This results in less tangling of leads and improved cable management.

To this point, many of the functional and software aspects of the invention have been described. Details of the hardware used in CMADAS 40 are shown in FIGS. 6–14.

Figure 6:
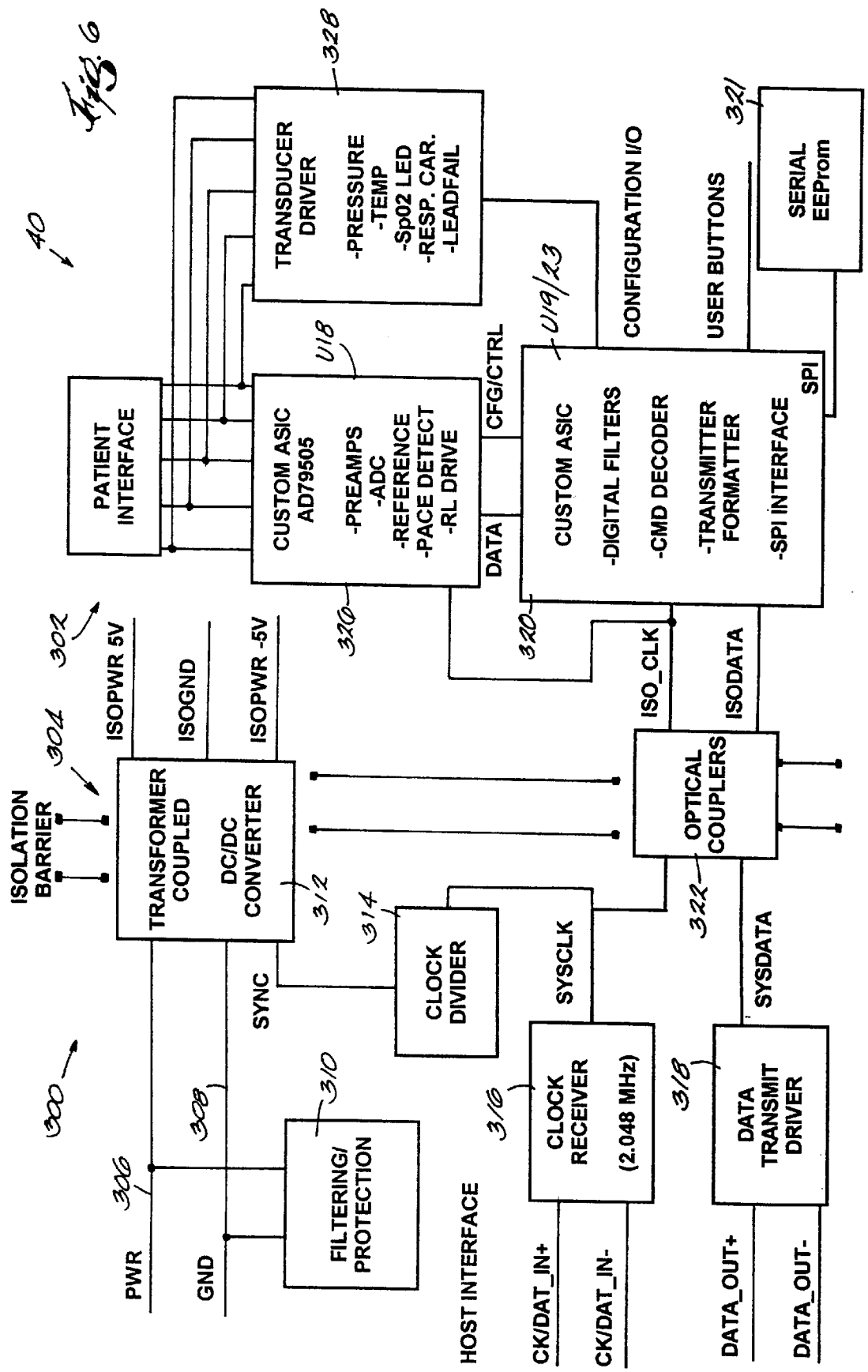
FIG. 6 is a block diagram of a cable management and data acquisition system of the invention.

FIG. 6 is a block diagram of the CMADAS 40. The CMADAS 40 is divided into two sections 300 and 302 by an isolation barrier 304. The section 300 includes power and ground inputs 306 and 308, a power filtering and protection circuit 310, a power transformer and converter 312, a clock divider 314, a clock receiver 316, and a data driver 318. The power transformer and converter 312 provides isolated low and high voltage power rails (in this case +5V and –5V) and a ground for the other components of the CMADAS. The clock receiver 316 and data driver 318 provide a communication link with the monitoring device 44 in the form of differential data inputs and outputs CK/DAT_IN+, CK/DAT_IN–, DATA_OUT+, DATA_OUT–. The clock receiver 316 transmits input data to a main processor 320 (which is equivalent to the ASIC 105 or 141) over a single line SYSCLK that is coupled to an optical isolation circuit 322. The optical isolation circuit 322 is coupled to the main processor 320 over a line ISO_CLK. Output data from the main processor 320 is delivered over a line ISODATA to the optical isolation circuit 322. The isolation circuit outputs corresponding isolated data over a SYSDATA line to the data receiver 318.

The section 302 of the CMADAS 40 includes the main processor 320, a sensor interface 324, a sensor driver and converter 326, and a sensor driver 328. The sensor interface 324 represents one or more of the connection ports 120, 122, 160, 162, and 164. The sensor driver and converter 326 performs several functions including pre-amplification, analog-to-digital conversion, and referencing of signals from the patient interface 324. The transducer driver 328 provides pre-amplification and processing of signals from specific sensors including pressure, temperature, blood oxygenation, respiratory, and failure signals.

Figure 7:
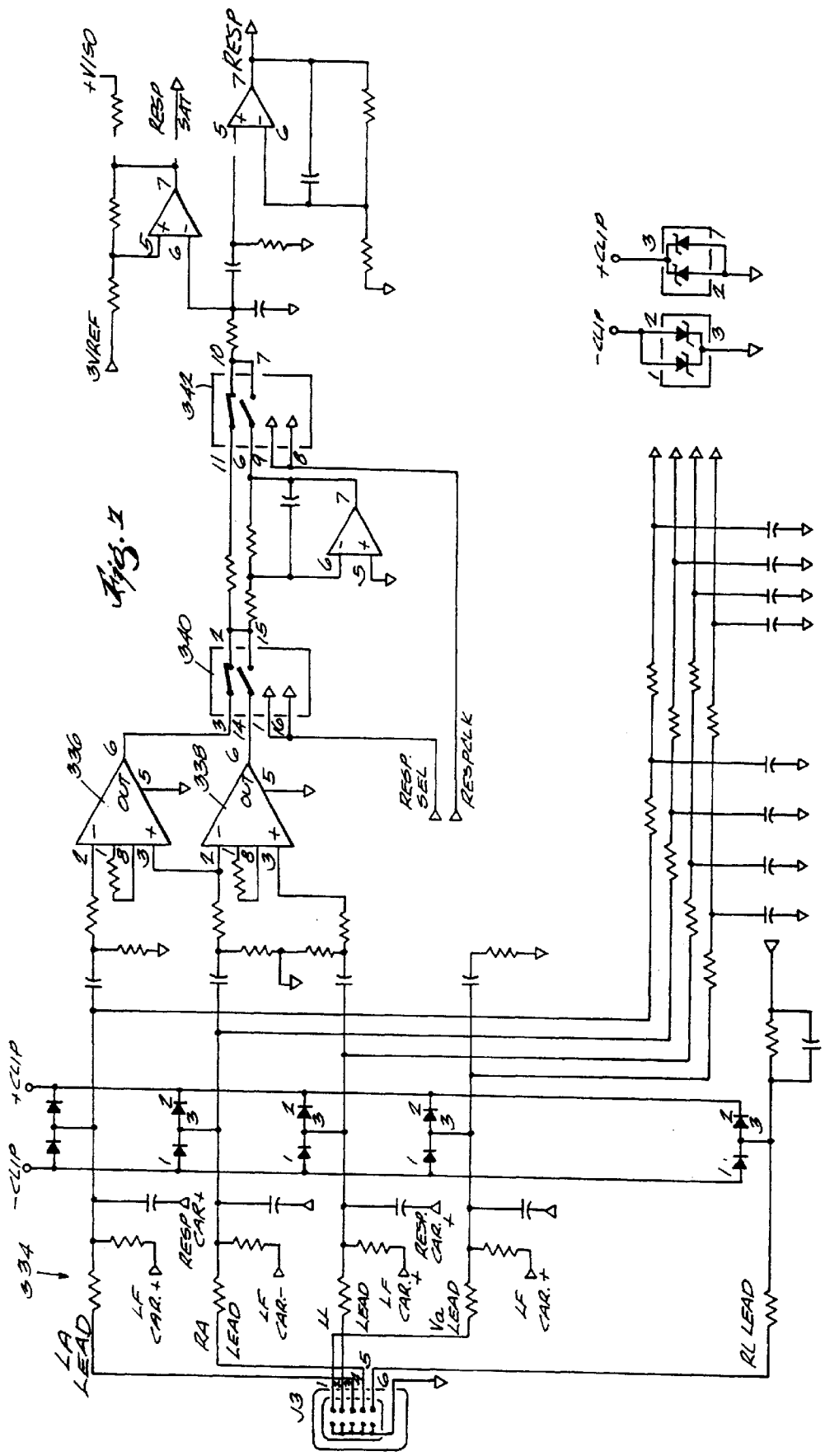
FIG. 7 is a circuit diagram of components of the sensor driver of the cable management and data acquisition system of FIG. 6.

FIG. 7 illustrates one of the components of the sensor driver 328. In particular, FIG. 7 illustrates an ECG/respiration interface 324. Signals from the LA, RA, and LL electrodes are processed in the driver. First, the signal from each of the three electrodes is mixed with a carrier signal. Subsequently, the signals are delivered to the differential amplifiers 336 and 338. The outputs of the two amplifiers 336 and 338 are processed in a lead select circuit 340 and a demodulator 342 to generate a respiratory signal RESP and a sensor saturation signal RESP_SAT. A signal from a $V_a$ electrode is similarly mixed with a carrier signal.

Figure 8:
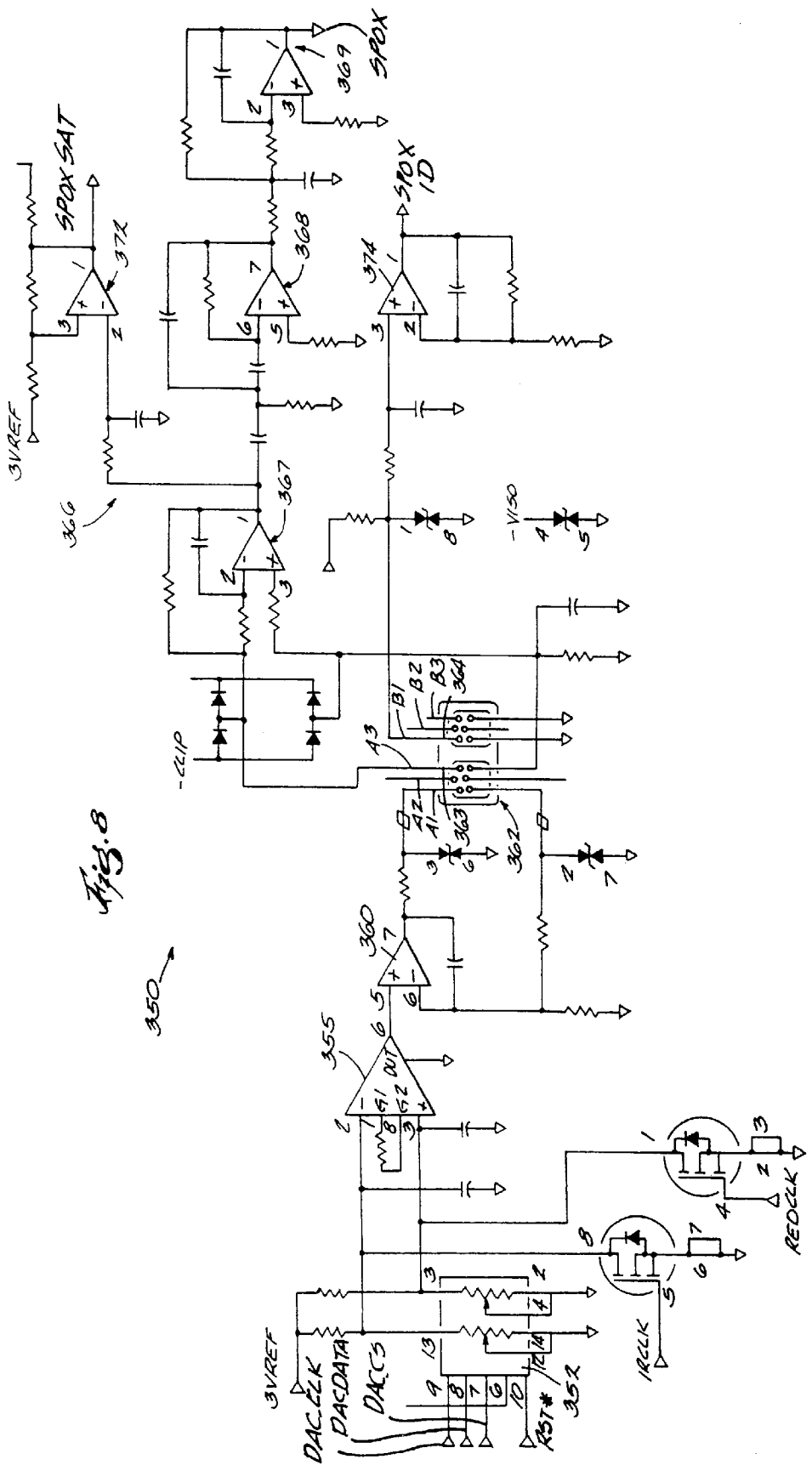
FIG. 8 is a circuit diagram of components of the transducer driver of the cable management and data acquisition system of FIG. 6.

FIG. 8 shows a driver/amplifier 350 for signals from a blood oxygenation sensor. The driver/amplifier 350 is a second component of the sensor driver 328 and includes a dual input LED driver amplifier having an input circuit 352, a differential amplifier 355, and a second amplifier 360. The output of the second amplifier 360 is delivered to a sensor connector 362 having a direct output 363 and a second output 364. The blood oxygenation sensor interfaces with the dual driver through the sensor connector 362. The output of the blood oxygenation sensor is delivered to, and processed by, a three-stage amplifier 366. The three-stage amplifier 366 includes a first stage 367, a second stage 368, and a third stage 369. The output of the first stage 367 is delivered to a saturation detector 372. The saturation detector 372 generates a saturation signal SPOX_SAT. The three-stage amplifier 366 also generates an output signal SPOX. A signal from the second output 364 of the connector 362 is delivered to an amplifier 374 that produces an identification signal SPOX_ID.

Figure 9:
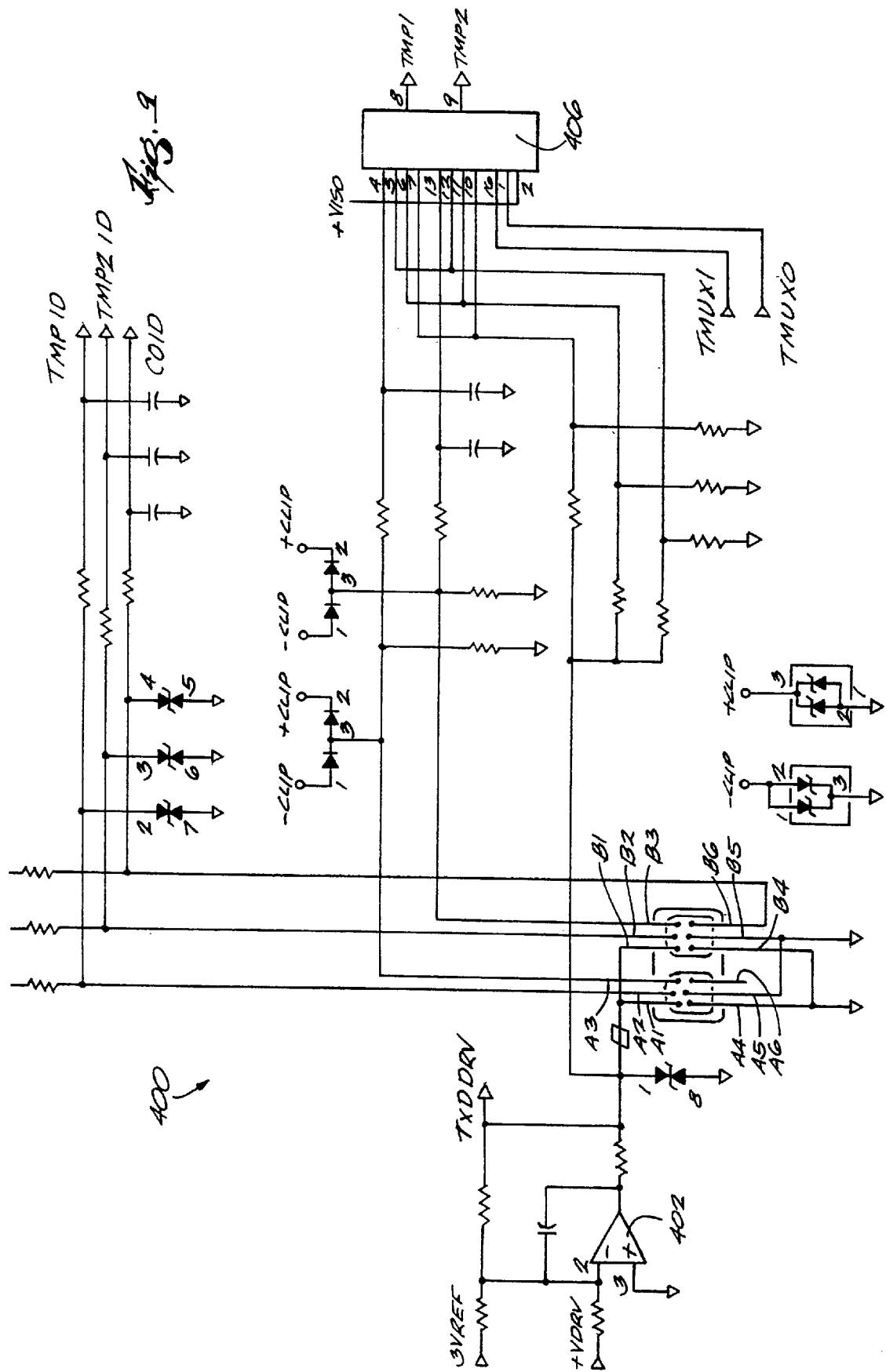
FIG. 9 is a circuit diagram of components of the transducer driver of the cable management and data acquisition system of FIG. 6.

FIG. 9 illustrates a circuit 400 used to drive dual-temperature sensors. Circuit 400 includes an amplifier 402 that generates a drive signal that is delivered to a temperature sensor connector 404. The connector 404 is coupled to a demultiplexer 406 that produces two drive signals TMP1 and TMP2. Three identification signals TMP1_ID, TMP2_ID and CO_ID are tapped from the isolation connector 404.

Figure 10:
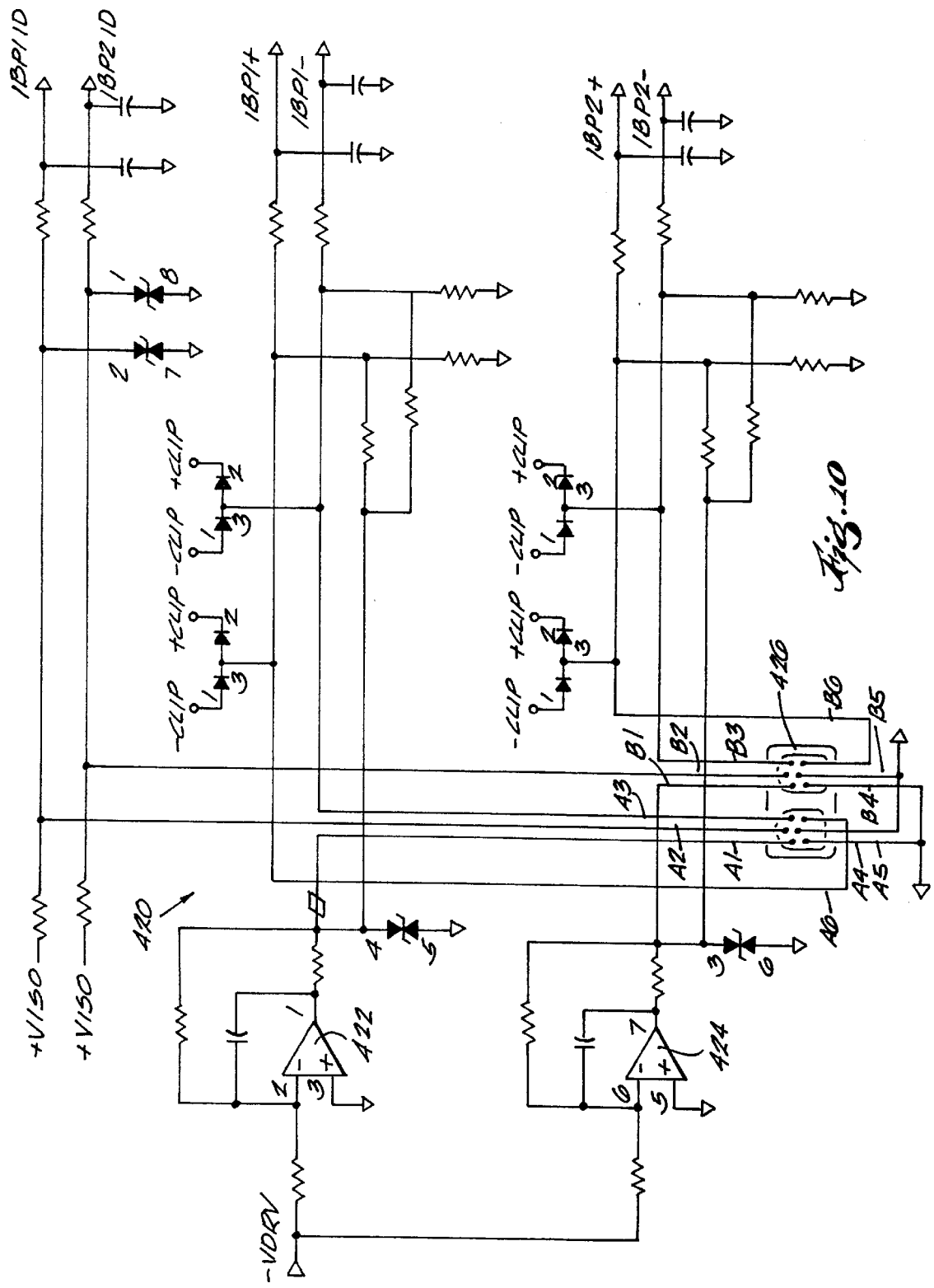
FIG. 10 is a circuit diagram of components of the transducer driver of the cable management and data acquisition system of FIG. 6.

FIG. 10 illustrates a circuit 420 used to drive blood pressure sensors. The circuit 420 includes two drive amplifiers 422 and 424. The outputs of each amplifier 422 and 424 are delivered to a connector 426. Taps off of the connector 426 are used to generate identification signals IPB1_ID, IBP2_ID, and differential signals IBP1+, IBP1–, IBP2+, and IBP2– for each sensor.

Figure 11:
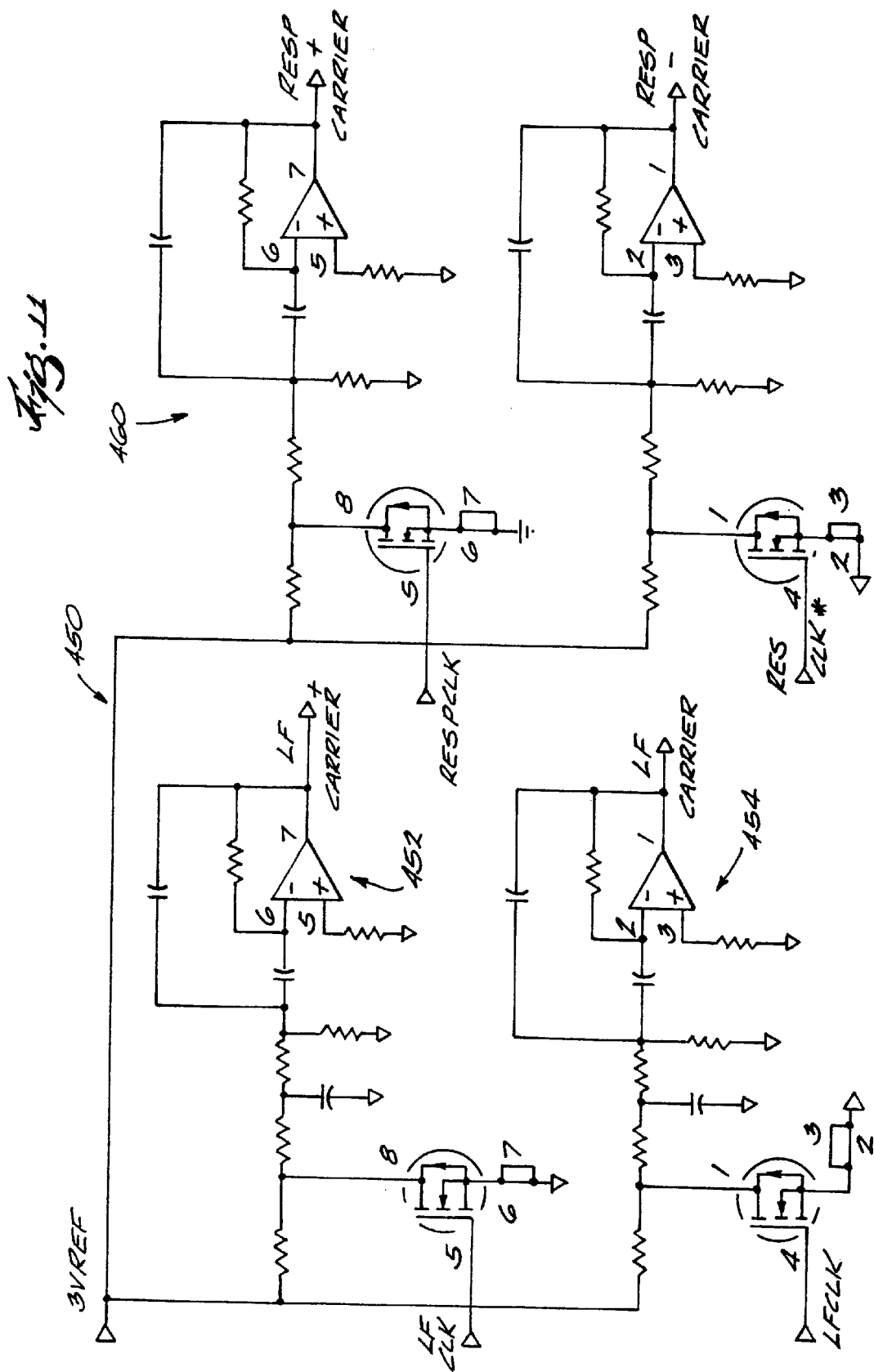
FIG. 11 is a circuit diagram of components of the transducer driver of the cable management and data acquisition system of FIG. 6.

FIG. 11 illustrates a drive circuit 450 designed to generate respiration ECG lead fail signals. The driver circuit 450 receives lead fail differential inputs LFCLK and LFCLK* (low). The signals are processed in transistor and amplifier circuits 452 and 454, respectively. The amplifiers 452 and 454 generate differential lead failure signals LF_CARRIER+ and LF_CARRIER–. A similar drive circuit 460 is used to generate differential respiratory carrier signals RESP_CARRIER+ and RESP_CARRIER–.

Figure 12:
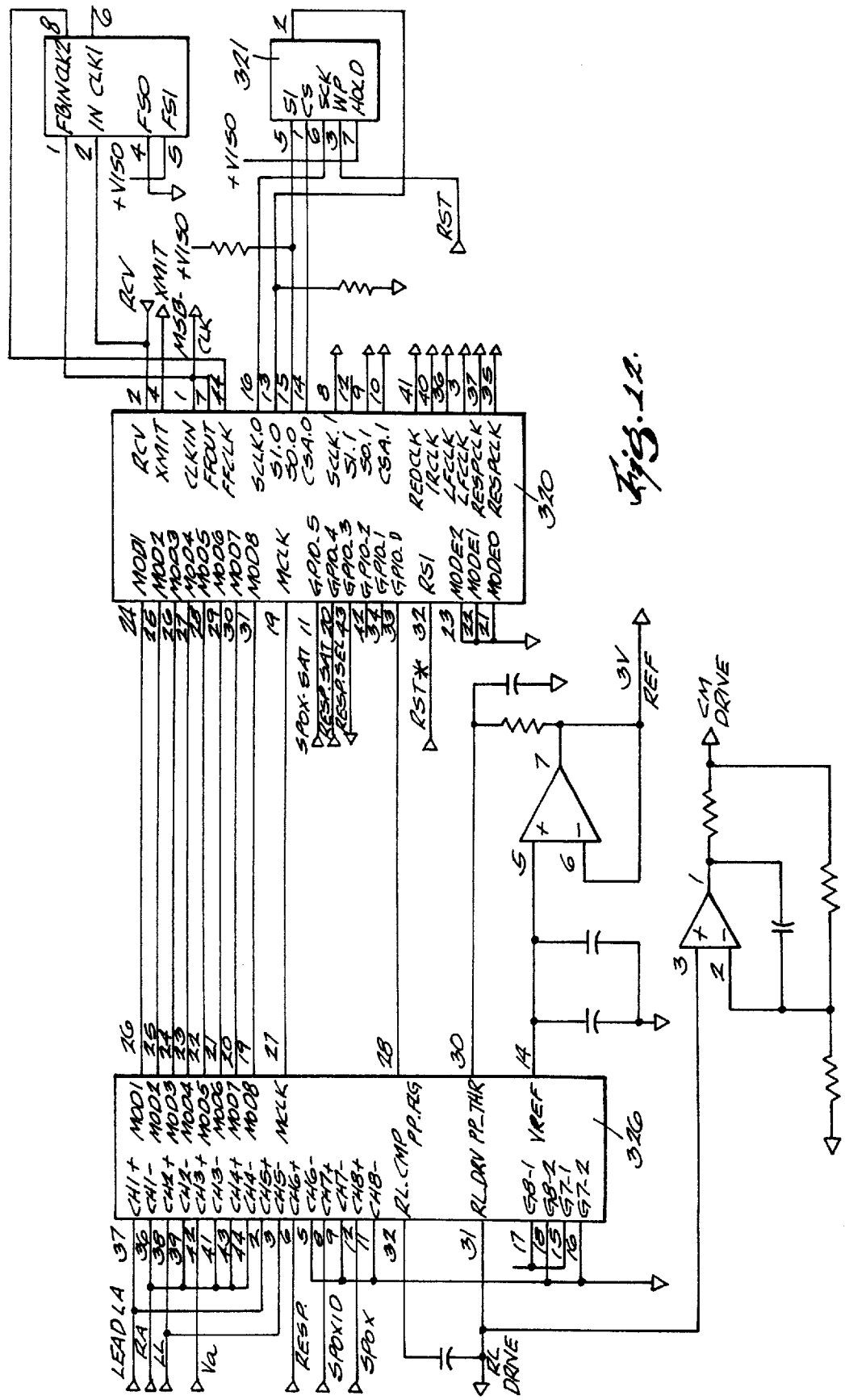
FIG. 12 is a circuit diagram of the driver and converter circuit and microprocessor of the cable management and data acquisition system of FIG. 6.

FIG. 12 is a detailed schematic of the sensor driver and converter 326 and the main processor 320. Signals from the LA, RA, LL and $V_a$ electrodes are processed by the sensor driver and converter 326. The main processor 320, using a phase-lock loop circuit 470 to control timing, processes the inputs and stores data in the memory 321, according to the scheme described above. The details of the sensor converter 326 are described in an article entitled "An 8-Channel, 18-Bit Data Acquisition System," published in CICC 1991, the disclosure of which is hereby incorporated by reference herein.

Figure 13:
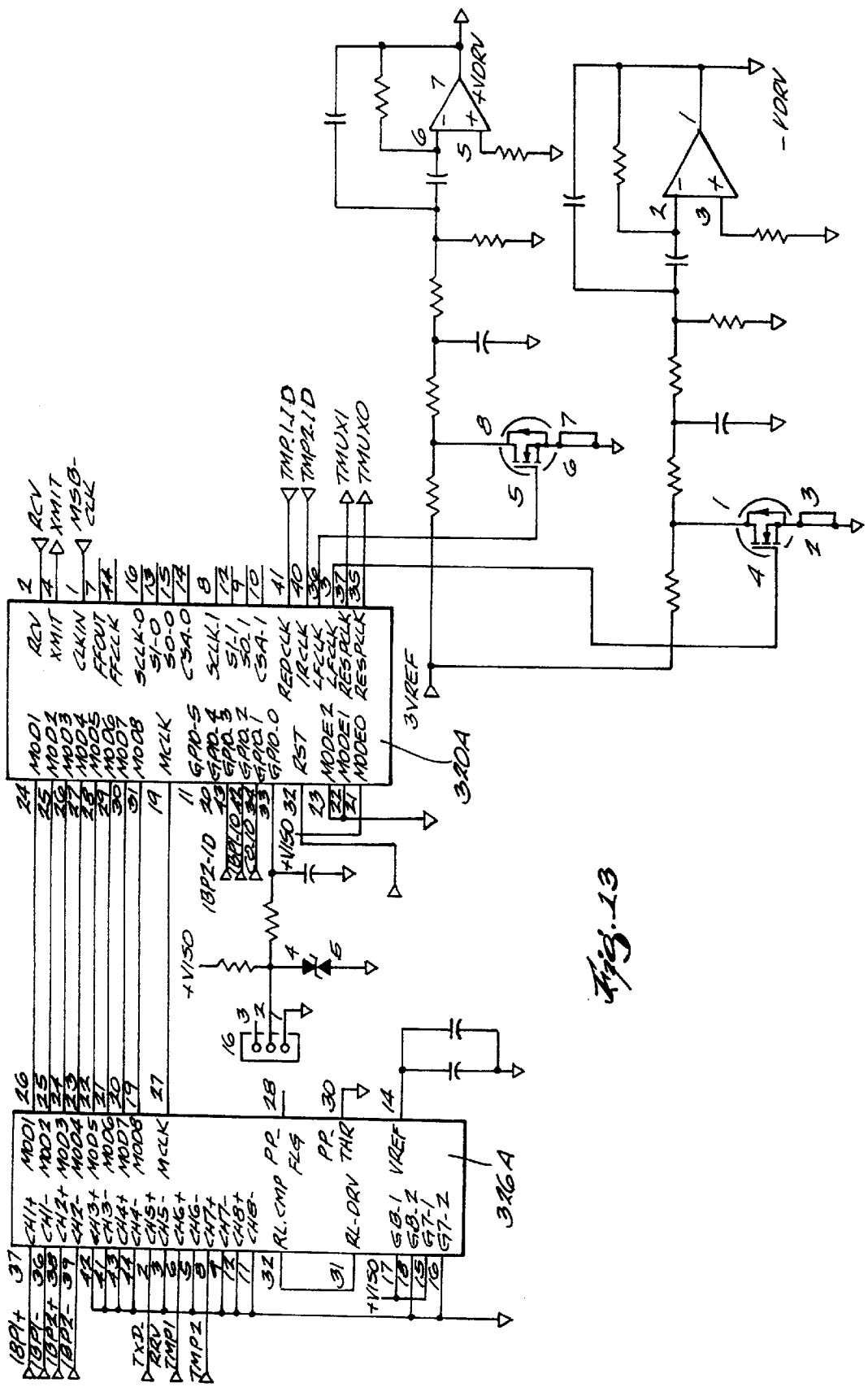
FIG. 13 is a circuit diagram of an additional embodiment of the invention where a second driver and converter circuit is coupled to the microprocessor of the cable management and data acquisition system.

FIG. 13 illustrates part of an optional embodiment of the invention with additional and parallel processing in the form of a second sensor driver and converter 326A and a second main processor 320A. The second sensor driver and converter 326A receives inputs from blood pressure and temperature sensors. That data is further processed in the second main processor 320A. The alternative embodiment of FIG. 13 also includes drive generator section 480 that is used to generate lead failure drive signals +VDRV and –VDRV.

Figure 14:
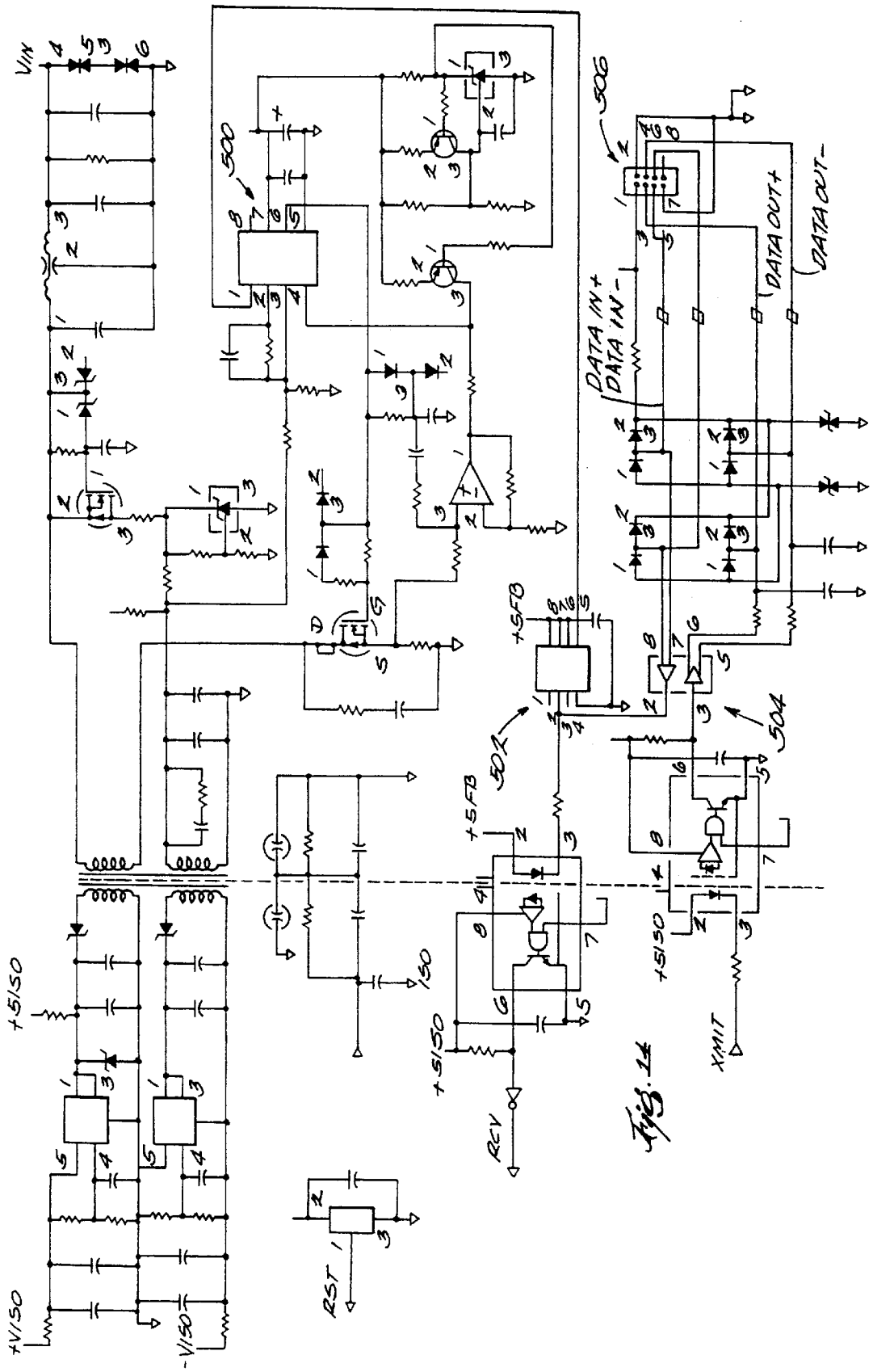
FIG. 14 is a circuit diagram of the power supply and sensor interface circuits of the cable management and data acquisition system of FIG. 6.

FIG. 14 further illustrates the power transformer and converter 312, the clock receiver 316, the clock divider 314, and the data transmit driver 318 circuits used in the presently preferred embodiment of the system. The power transformer and converter 312 is a switch-mode power supply, with an AC-to-AC converter 500. The remaining details of the power transformer and converter 312 should be readily apparent to one of ordinary skill in the art and are not discussed in further detail herein. The clock divider 314 includes a standard clock divider IC 502. The clock receiver 316 includes one half of a receiver-driver IC 504. The data transmit driver 318 includes the other half of the receiver-driver IC 504. A connector 506 provides an interface for the sensor leads (not shown in FIG. 14). The connector 506 also connects to the CK/DAT_IN+, CK/DAT_IN−, DATA_OUT+, and DATA_OUT−lines, respectively.

As can be seen from the above, the invention provides a method and apparatus for preventing data loss when a patient monitoring system is disconnected from monitoring sensors. The invention also provides improved routing of sensor cables.

Various features and advantages of the invention are set forth in the following claims.

What is claimed is:

1. A cable management device comprising:
    a housing;
    a first connection port operable to receive information from a first sensor;
    a device interface coupled to the first connection port;
    a non-volatile memory coupled to the device interface;
    an output port coupled to the device interface;
        wherein the device interface communicates information according to a hot-swappable serial data bus protocol.

2. An information acquisition system comprising:
    a monitoring processor to generate read and write messages;
    a signal processor coupled to the monitoring processor and operable to execute read and write messages from the monitoring processor; and
    a cable management device operable to be coupled to the signal processor and located in a housing separate from the monitoring processor, the cable management device having
        a first connection port operable to receive information from at least one sensor,
        a data storage device operable to store data based on information sensed by the at least one sensor,
        a device interface coupled to the first connection port and the signal processor, and
        an output port coupled to the device interface.

3. A system as claimed in claim 2, wherein the monitoring processor includes a memory package.

4. A system as claimed in claim 3, wherein the memory package includes a request message sub-package and an algorithm sub-package.

5. A system as claimed in claim 4, wherein the monitoring processor includes a communications controller that generates message packets.

6. A system as claimed in claim 5, wherein the request message sub-package assembles message packets.

7. A system as claimed in claim 6, wherein the request message sub-package validates assembled message packets.

8. A system as claimed in claim 2, wherein the cable management device further comprises a second connection port.

9. A system as claimed in claim 2, wherein the cable management device further comprises a housing.

10. A method of storing patient data, the method comprising:
    gathering data from at least one sensor;
    generating a write command with a monitoring processor;
    processing the write command in a signal processor;
    executing the write command through a device interface;
    locating a non-volatile memory outside the sensor and outside the monitoring processor;
    storing the gathered data in the non-volatile memory;
    wherein processing the write command includes processing the command in a request message sub-package.

11. A method of storing patient data, the method comprising:
    gathering data from at least one sensor;
    generating a write command with a monitoring processor;
    processing the write command in a signal processor;
    executing the write command through a device interface;
    locating a non-volatile memory outside the sensor and outside the monitoring processor;
    storing the gathered data in the non-volatile memory;
    wherein processing the write command includes processing the command in a request message sub-package, and where processing the write command includes processing the command in an algorithm sub-package.

12. A method of storing patient data, the method comprising:
    gathering data from at least one sensor;
    generating a write command with a monitoring processor;
    processing the write command in a signal processor;
    executing the write command through a device interface;
    locating a non-volatile memory outside the sensor and outside the monitoring processor;
    storing the gathered data in the non-volatile memory;
        wherein processing the write command includes setting bus commands from a command table.

* * * * *